United States Patent
Hunt et al.

(10) Patent No.: US 9,886,730 B2
(45) Date of Patent: *Feb. 6, 2018

(54) SYSTEMS AND METHODS FOR OBTAINING MEDICAL INFORMATION

(71) Applicant: Endevr LLC, St. George, UT (US)

(72) Inventors: Brandon Hunt, St. George, UT (US); Josh Taylor, St. George, UT (US)

(73) Assignee: Endevr LLC, St. George, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/162,378

(22) Filed: May 23, 2016

(65) Prior Publication Data

US 2016/0267617 A1  Sep. 15, 2016

Related U.S. Application Data

(63) Continuation of application No. 14/537,271, filed on Nov. 10, 2014, now Pat. No. 9,361,657, which is a
(Continued)

(51) Int. Cl.
*G06K 19/06* (2006.01)
*G06Q 50/24* (2012.01)
(Continued)

(52) U.S. Cl.
CPC ........... *G06Q 50/24* (2013.01); *A44C 5/0015* (2013.01); *G06F 17/30879* (2013.01);
(Continued)

(58) Field of Classification Search
CPC .............................. G06K 7/1417; G06Q 50/24
(Continued)

(56) References Cited

U.S. PATENT DOCUMENTS

| 3,864,856 A | 2/1975 | McManus |
| 4,857,716 A | 8/1989 | Gombrich et al. |

(Continued)

FOREIGN PATENT DOCUMENTS

| JP | 2002083062 A | 3/2002 |
| JP | 2003036313 A | 7/2003 |

(Continued)

OTHER PUBLICATIONS

Written Opinion for PCT/US2013/058150, dated Sep. 5, 2013, 7 pgs.

(Continued)

*Primary Examiner* — Seung Lee
(74) *Attorney, Agent, or Firm* — Phillips Ryther & Winchester; Matthew D. Thayne

(57) ABSTRACT

Methods for communicating medical information using a wearable item, such as a bracelet, comprising a QR code. In some implementations, the wearable medical item comprises a backup telephone number for obtaining medical information related to a wearer of the medical item and a security code and/or patient ID. Upon receiving a telephone call at the backup telephone number and receiving the security code and/or the patient ID and validation of the security code and/or the patient ID, medical information related to the wearer of the wearable medical item may be received, which may provide for a backup way of obtaining the medical information in the event that a first responder or other person accessing the wearable item cannot scan the QR code.

20 Claims, 5 Drawing Sheets

Related U.S. Application Data continuation of application No. 13/606,562, filed on Sep. 7, 2012, now Pat. No. 8,881,990.

(51) Int. Cl.

| | |
|---|---|
| G09F 3/00 | (2006.01) |
| A44C 5/00 | (2006.01) |
| G06K 19/077 | (2006.01) |
| G06F 19/00 | (2011.01) |
| G06K 7/10 | (2006.01) |
| G06F 17/30 | (2006.01) |
| H04M 3/51 | (2006.01) |

(52) U.S. Cl.
CPC ....... *G06F 19/323* (2013.01); *G06K 7/10891* (2013.01); *G06K 19/06037* (2013.01); *G06K 19/07762* (2013.01); *G09F 3/005* (2013.01); *G06F 17/30861* (2013.01); *H04M 3/5116* (2013.01); *H04M 2242/04* (2013.01)

(58) Field of Classification Search
USPC .......................................................... 235/494
See application file for complete search history.

(56) References Cited

U.S. PATENT DOCUMENTS

| | | |
|---|---|---|
| 5,877,742 A | 3/1999 | Klink |
| 6,073,106 A * | 6/2000 | Rozen .................. G06F 19/323 705/2 |
| 7,696,880 B2 | 4/2010 | Carmeli et al. |
| 8,135,597 B1 | 3/2012 | Tahan |
| 8,819,837 B2 | 8/2014 | Lacey |
| 8,881,990 B2 | 11/2014 | Hunt et al. |
| 2003/0016122 A1 | 1/2003 | Petrick |
| 2007/0203751 A1 | 8/2007 | Koblasz |
| 2011/0093296 A1 | 4/2011 | Klink |
| 2012/0049505 A1 | 3/2012 | Yokoyama |
| 2013/0126601 A1 | 5/2013 | Lee |
| 2013/0268292 A1 | 10/2013 | Kim et al. |
| 2013/0290013 A1 | 10/2013 | Forrester |

FOREIGN PATENT DOCUMENTS

| | | |
|---|---|---|
| KR | 200459026 | 3/2012 |
| WO | WO2014039614 | 3/2014 |

OTHER PUBLICATIONS

International Search Report for PCT/US2013/058150, dated Sep. 5, 2013, 3 pgs.
JP2003036313A—Machine Translation of Application.
KR200459026—Machine Translation of Application.

\* cited by examiner

PRIOR ART

George W. Jones

Address
Phone
Email

Emergency Contacts

Vitals
   Gender
   DOB
   Height/Weight
   Blood Type
   Donor

Medical Profile
  MAJOR MEDICAL CONDITION
   Allergies
   Meds

Insurance

Physicians

SYSTEMS AND METHODS FOR OBTAINING MEDICAL INFORMATION

RELATED APPLICATIONS

This is a continuation of co-pending U.S. patent application Ser. No. 14/537,271, titled "SYSTEM AND METHOD FOR QUICKLY OBTAINING MEDICAL INFORMATION," which was filed on Nov. 10, 2014, which is a continuation of U.S. patent application Ser. No. 13/606,562, titled "SYSTEM AND METHOD FOR QUICKLY OBTAINING MEDICAL INFORMATION," which was filed on Sep. 7, 2012, and is now issued as U.S. Pat. No. 8,881,990, each of which is hereby incorporated by reference in its entirety.

FIELD OF THE INVENTION

The present invention relates generally to emergency medical identification devices and more particularly to a system and method for quickly obtaining a person's medical information using a QR code on a wristband or other worn object.

DESCRIPTION OF THE PRIOR ART

It is well-known in the art for people to wear wrist bands containing medical information. For example, diabetics have worn bands or carried tags to notify of their illness since there is a certain probability that the diabetic might be found unconscious. For years, patient identification has been placed on a bracelet or wrist-band known as a MEDICALERT bracelet or pendent. This is well known to ER and first-responder personnel, and it is one of the first things they look for. However, a MEDICALERT device usually only provides a telephone number that can be called for the patient's medical information.

U.S. published application 2011/0093296 describes a device that resembles a wristwatch that can store and instantly display complete medical information about a patient.

U.S. Pat. No. 3,864,856 teaches medical information being on a card held in a compartment of a watch or wrist-strap.

U.S. Pat. No. 5,877,742 teaches a medical identification bracelet that has electronic circuitry to display detailed patient medical information.

U.S. published application no. 2003/0016122 teaches an RFID tag worn by a person that transmit coded information allowing access to medical information.

The United States Dept. of Health and Human Services is calling for national coordination for health information technology. The government is proposing electronic wrist-bands that can contain information on over 125 chronic medical conditions.

The problem with electronic wrist-bands or other electronic devices is that they require periodic battery replacement or charging, are subject to damage from blows or shocks, and will usually not function after being placed in water. It would be advantageous to have a wrist-band that did NOT contain any electronics, but could harness the power of the modern electronic/telecommunications world, especially the cellular telephone or smartphone, to immediately retrieve critical medical information by first responders and ER teams.

A QR code (Quick Response Code) is well-known and heavily used today. A QR code is a small square coded patch (see FIG. 2) resembling a 2-dimensionsal bar code (but different) that is designed to be viewed by the camera or image sensor in a cellular smartphone, pad or other portable device. Typically, the QR code simply returns a URL that the user's browser then moves to. Alternatively, QR codes can be used to initiate the downloading of applications (Apps.).

[Unlike the older bar codes that were designed to be mechanically scanned by a narrow beam of light, the QR code is detected as a 2-dimensional digital image by a semiconductor image sensor and is then digitally analyzed by a programmed processor. The processor locates three distinctive squares at the corners of the image, normalizes image size, orientation, and angle of viewing with the aid of a smaller square near the fourth corner. The small dots are then converted to binary numbers and validity checked with an error-correcting code.] (From Wikipedia.com).

Since most first responders and ER personnel carry cellular telephones, and especially smartphones, and because almost every future cellular telephone will be able to read a QR code, it would be very advantageous to combine the quick access and response of a QR code with a medical bracelet or wrist-band, or any other worn item that can hold a QR code.

SUMMARY

The present invention relates to a new type of medical bracelet, wrist-band device, watch, piece of jewelry (or any other worn item) that displays a QR code for fast scanning by first responders, ER teams or any other medical personnel. Scanning the QR code with a telephone or other handheld device results in immediate retrieval of pertinent medical information from a dedicated website or directly from the QR code itself. Further security of information can be provided by a numerical or alphanumerical patient ID and a PIN that can be printed on the device for fast access.

The device can be a simple bracelet, or it can be a stylish piece of jewelry by having a designer shape. It can also being a man's or woman's wristwatch, a pendent, a piece of jewelry, or any other worn item including an ion or negative ion bracelet, or magnet bracelet known in the art.

The inside or outside of the device can have a highly visible, and easily scanable, QR code. It can also have instructions to scan for medical information, a patient ID, a PIN number and/or a telephone number that can be called as a backup. Other optional information can be included.

DESCRIPTION OF THE FIGURES

Attention is now directed at several drawings that illustrate features of the present invention.

Several drawings and illustrations have been presented to aid in understanding the present invention. The scope of the present invention is not limited to what is shown in the figures.

DETAILED DESCRIPTION

The present invention relates to a medical wrist-band, bracelet, watch, piece of jewelry, pendent, necklace or any other worn device holding a QR code for fast scanning to obtain emergency medical information about the wearer.

Figure 1:
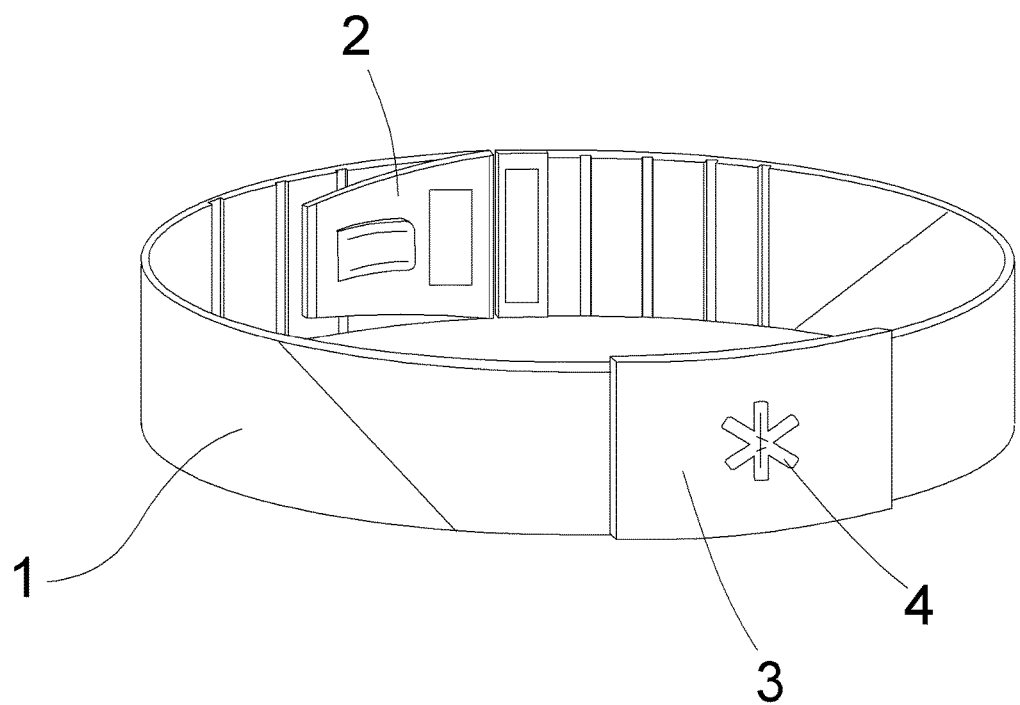
FIG. 1 shows a profile view of a wrist-band embodiment of the present invention.

FIG. 1 shows a wrist-band embodiment of the invention. A band 1 buckles around the wrist 2 and carries a tag 3 optionally displaying a medical symbol 4. The inside of the tag 3 displays a QR code along with supplementary information.

Figure 2:
FIG. 2 shows a prior art QR code.

FIG. 2 shows a prior art QR code. The code has three alignment symbols which can be seen in FIG. 2 as larger squares on the upper and lower left side and the right top. QR codes follow one of a family of standards, and are readable by millions of smart telephones today. In the future, almost every handheld telephone, pad device or computer will be able to scan and read them.

According to Wikipedia, [QR codes, formerly confined to industrial uses, have in recent years become common in consumer advertising and packaging. Users with a camera phone equipped with the correct reader application can scan the image of the QR Code to display text, contact information, connect to a wireless network or open a web page in the telephone's browser. QR Codes may also be linked to a location to track where a code has been scanned. The application that scans the QR Code can also optionally retrieve geographic information by using the GPS receiver in the telephone].

Figure 3:
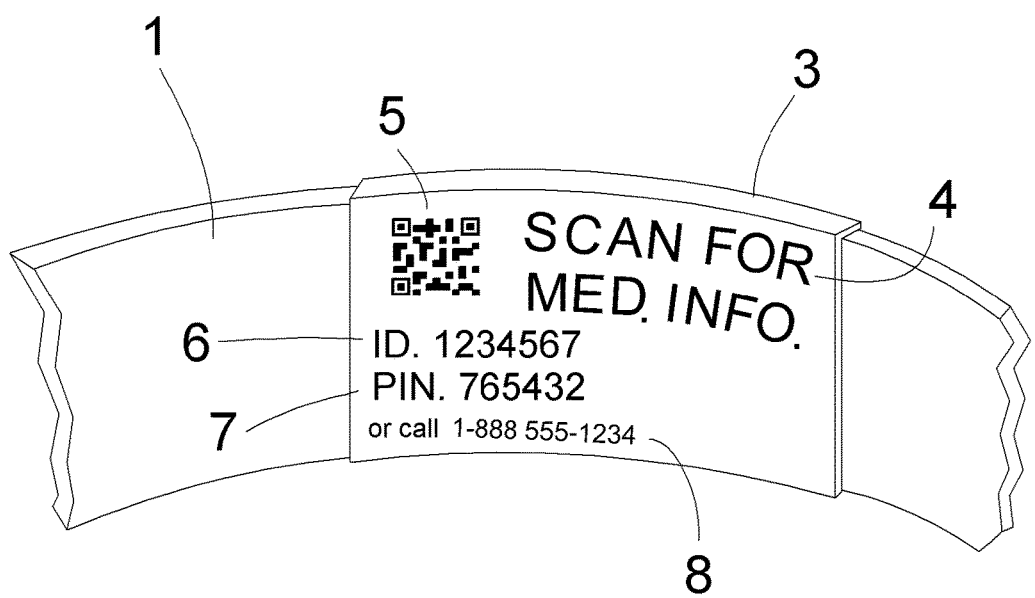
FIG. 3 shows the inside of the wrist-band tag from FIG. 1 with the QR code visible.

FIG. 3 shows the inside of the tag 3 in the wrist-band embodiment of FIG. 1. The tag 3 can display a QR code 5, instructions to scan 4 (so that a responder knows he or she will receive medical information), an optional patient ID 6, an optional PIN 7 and an optional backup telephone number 8.

Upon scanning the QR code 5, the responder may be supplied with one or both of two different types of information. The first type is information encoded in the QR code itself. Newer versions of QR codes can contain much more information than older versions. The second type of information is the URL of a webpage. The responder's online browser can immediately go to that webpage.

The first type of information might be a simple message identifying a major condition such as "DIABETIC" or it might be more detailed. The second type of information can be detailed medical information from a database provided on the webpage. The present invention allows one or both types of information to be supplied to the responder. In the case of a webpage, the responder can query the webpage for further information if necessary.

When a webpage is used, extremely important information about that patient could be supplied instantly by the website upon entry. This can be accomplished by encoding the patient ID and optionally the PIN in the QR code itself. Alternatively, the responder could be asked to enter the patient ID and PIN, or, in some embodiments, only the patient ID. The tradeoff is security of patient information against speed in which the responder can obtain necessary information. Encryption of information in the QR code or of information transmitted or stored on the website can be used to enhance security.

Figure 4:
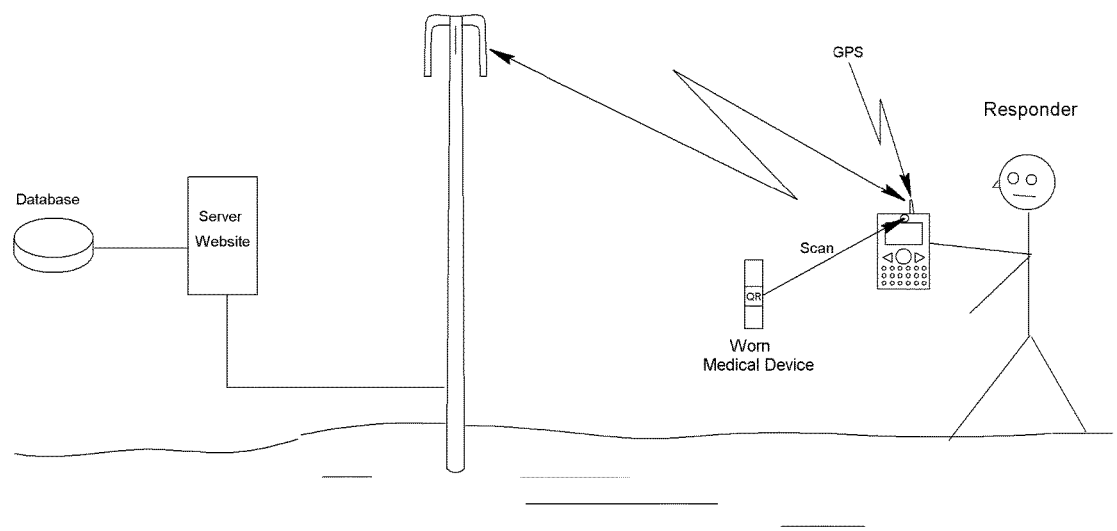
FIG. 4 shows the transmission of location information after scanning.

The webpage service can also optionally provide hospital pre-notification that the QR code has been scanned by a particular responder. Alternatively, the responder can initiate hospital pre-notification on the webpage. In some embodiments of the invention, the telephone can determine the geographic location of the responder at the time the QR code is scanned (using the telephone's GPS or other location services). This location data could be forwarded along with hospital pre-notification. A database provided either by the website or the App. in the telephone could choose (or be preprogrammed with) the correct hospital where the patient will be taken based on geographic location. This is shown in FIG. 4. A responder scans the QR code, which returns a URL. Geographic information is sent to the website, and medical information is sent from the website to the responder.

The backup telephone number on the worn device could be answered by a 24 hours emergency call center. In this case, a live person can provide data to the responder and optionally hospital pre-notification.

Figure 5:
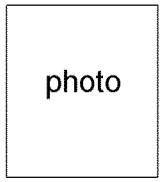
FIG. 5 shows the display that can be returned to a responder after scanning.

The webpage can be supplied in a form that is easily readable on a cellular telephone. An example of this is shown in FIG. 5. Here, the returned profile has the person's name, photo, address, phone, email, emergency contacts, vitals, medical profile including MAJOR MEDICAL CONDITIONS, allergies and medications, insurance information and names and address of physicians. Many variations are possible; however, FIG. 5 illustrates the basic layout of a returned webpage. Any format or content of a returned webpage is within the scope of the present invention.

The user, when not in an emergency situation, can easily logon to the website to update their patient information. Doctors and other healthcare professionals can also optionally logon to the website to update patient data. Alternatively, patient data could be transferred to the website (with permission of the patient) from a physician's or hospital's database. This type of information entry or transfer is particularly important to make sure the medications currently being taken by the patient are correctly entered since many drugs have similar, but slightly different names.

In different embodiments of the present invention, the QR code can be displayed on the outside of the device for quicker access, or on both the inside and outside.

While most smartphones have applications (Apps.) that can already scan a QR code and access a URL, the present invention can also supply custom applications to responders to carry in there telephones. The specialized Apps. could display local information contained in the QR code and perform other services such as sending location information as has been discussed.

Some embodiments of the invention can have more than one QR code so that more data can be put into the QR code for use by responders. Maximum local information is particularly important for emergencies such as hurricanes, tornadoes, floods and other natural disasters that affect large numbers of people and may take both electricity and cellular service down. In these cases, the telephone browser may not work, and websites may not be accessible. However, as long as the telephone has battery power, it can scan the QR code and display the information stored in the code. This locally stored and displayed information can be the essential medical information needed by the responder.

The present invention is a system and method that can vastly speed up the flow of emergency medical information into the hands of first responders and ER teams by using a quickly and easily scanned QR code on a worn device like a bracelet, watch or piece of jewelry.

Several descriptions and illustrations have been provided to aid in understanding the present invention. One with skill in the art will realize that numerous changes and variations may be made without departing from the spirit of the invention. Each of these changes and variations is within the scope of the present invention.

The invention claimed is:

1. A method for receiving medical information, the method comprising the steps of:
  accessing a wearable medical item by a first responder during a medical emergency, wherein the wearable medical item comprises a QR code, wherein the QR code comprises an embedded URL, wherein the URL contains medical information related to a wearer of the medical item, and wherein the wearable medical item further comprises a backup telephone number for obtaining medical information related to the wearer of the medical item;
  upon determining that the QR code cannot be scanned, calling the backup telephone number; and
  receiving medical information related to the wearer of the wearable medical item from the backup telephone number.

2. The method of claim 1, wherein the wearable medical item further comprises a security code.

3. The method of claim 2, wherein the security code comprises a PIN number.

4. The method of claim 2, further comprising providing the security code during the call to the backup telephone number.

5. The method of claim 4, wherein the step of providing the security code comprises entering the security code on a keypad.

6. The method of claim 4, further comprising providing a patient ID during the call to the backup telephone number, wherein the patient ID identifies the wearer of the wearable medical item.

7. The method of claim 6, wherein the patient ID is printed on the wearable medical item.

8. The method of claim 1, wherein the wearable medical item comprises at least one of a bracelet, a wrist-band device, a watch, and a piece of jewelry.

9. The method of claim 8, wherein the wearable medical item comprises a bracelet.

10. The method of claim 1, wherein the step of receiving medical information comprises receiving the medical information from an operator contacted using the backup telephone number.

11. The method of claim 1, further comprising attempting to scan the QR code on a handheld device.

12. The method of claim 1, wherein the step of, upon determining that the QR code cannot be scanned, calling the backup telephone number, comprises, upon determining that the QR code cannot be scanned because the first responder lacks a handheld device capable of scanning the QR code, calling the backup telephone number.

13. A method for communicating medical information, the method comprising the steps of:
  providing a wearable medical item comprising a QR code, wherein the QR code comprises an embedded URL, wherein the URL contains medical information related to a wearer of the medical item, and wherein the wearable medical item further comprises a backup telephone number for obtaining medical information related to the wearer of the medical item and at least one of a security code and a patient ID;
  receiving a telephone call at the backup telephone number;
  receiving at least one of the security code and the patient ID; and
  upon validation of at least one of the security code and the patient ID and without receipt of information from the QR code, relaying medical information related to the wearer of the wearable medical item.

14. The method of claim 13, wherein the step of relaying medical information related to the wearer of the wearable medical item comprises relaying medical information related to the wearer of the wearable medical item from an operator contacted using the backup telephone number.

15. The method of claim 13, wherein the step of relaying medical information related to the wearer of the wearable medical item comprises sending medical information electronically.

16. The method of claim 13, wherein the step of receiving a telephone call at the backup telephone number comprises receiving a telephone call at the backup telephone number as a backup in the event that the QR code cannot be scanned.

17. The method of claim 13, wherein the wearable medical item comprises a security code printed on the wearable medical item.

18. The method of claim 17, wherein the security code comprises a PIN number.

19. A method for communicating medical information to first responders, the method comprising the steps of:
  providing a wearable medical bracelet, wherein the wearable medical bracelet comprises:
    a QR code comprising an embedded URL, wherein the URL contains medical information related to a wearer of the medical item;
    a backup telephone number for obtaining medical information related to the wearer of the medical item;
    a patient ID associated with the wearer of the medical item; and
    a security code;
  receiving a telephone call at the backup telephone number from a first responder during a medical emergency as a backup in the event that the QR code cannot be scanned;
  receiving the patient ID;
  receiving the security code; and
  upon validation of the patient ID and the security code, relaying medical information related to the wearer of the wearable medical item.

20. The method of claim 19, wherein the security code comprises a PIN number.

* * * * *